(12) United States Patent
Jarva et al.

(10) Patent No.: US 10,863,951 B2
(45) Date of Patent: Dec. 15, 2020

(54) COMPUTED TOMOGRAPHY AND POSITIONING OF THE ANATOMY DESIRED TO BE IMAGED

(71) Applicant: PLANMECA OY, Helsinki (FI)

(72) Inventors: Mikko Jarva, Helsinki (FI); Kustaa Nyholm, Helsinki (FI)

(73) Assignee: Planmeca OY, Helsinki (FI)

( * ) Notice: Subject to any disclaimer, the term of this patent is extended or adjusted under 35 U.S.C. 154(b) by 0 days.

(21) Appl. No.: 16/475,183

(22) PCT Filed: Dec. 15, 2017

(86) PCT No.: PCT/FI2017/050902
§ 371 (c)(1),
(2) Date: Jul. 1, 2019

(87) PCT Pub. No.: WO2018/122451
PCT Pub. Date: Jul. 5, 2018

(65) Prior Publication Data
US 2019/0336087 A1 Nov. 7, 2019

(30) Foreign Application Priority Data
Dec. 30, 2016 (FI) .................................. 20160295

(51) Int. Cl.
*G06K 9/00* (2006.01)
*A61B 6/04* (2006.01)
(Continued)

(52) U.S. Cl.
CPC ................ *A61B 6/04* (2013.01); *A61B 6/032* (2013.01); *A61B 6/08* (2013.01); *A61B 6/14* (2013.01);
(Continued)

(58) Field of Classification Search
CPC . A61B 34/10; A61B 34/20; A61B 2034/2068; A61B 2034/107;
(Continued)

(56) References Cited

U.S. PATENT DOCUMENTS

| 2008/0181356 A1 | 7/2008 | Sukovic et al. |
| 2009/0088830 A1* | 4/2009 | Mohamed ................. A61F 2/91 623/1.11 |

(Continued)

FOREIGN PATENT DOCUMENTS

| EP | 2130491 A1 | 9/2009 |
| WO | 2016156150 A1 | 10/2016 |

OTHER PUBLICATIONS

International Search Report for PCT/FI2017/080902, dated Apr. 4, 2018, 4 pages.

*Primary Examiner* — Don K Wong
(74) *Attorney, Agent, or Firm* — Fay Sharpe LLP

(57) ABSTRACT

The invention relates to a problem of setting mutual position of an anatomy being imaged and imaging means of a computed tomography imaging apparatus so that specifically the very volume of the anatomy desired to be imaged actually is imaged. To further the positioning, a positioning tool in a form of a three-dimensional virtual positioning model (40), generated from the anatomy to be imaged, is shown on a display from which the volume (41) of the anatomy desired to be imaged can be pointed, selected or defined.

20 Claims, 3 Drawing Sheets

(51) Int. Cl.
  *A61B 6/03* (2006.01)
  *A61B 6/08* (2006.01)
  *A61B 6/14* (2006.01)
  *A61B 6/00* (2006.01)
  *G06T 15/08* (2011.01)
  *H04N 5/247* (2006.01)

(52) U.S. Cl.
  CPC ............. *A61B 6/501* (2013.01); *A61B 6/54* (2013.01); *G06T 15/08* (2013.01); *G06T 2210/41* (2013.01); *H04N 5/247* (2013.01)

(58) Field of Classification Search
  CPC ........ A61B 2090/376; A61B 2034/105; A61B 2034/108; A61B 2090/3762; A61B 2090/371; A61B 5/742; A61B 8/483
  See application file for complete search history.

(56) References Cited

U.S. PATENT DOCUMENTS

| | | |
|---|---|---|
| 2011/0129058 A1 | 6/2011 | Ulrici et al. |
| 2016/0174916 A1 | 6/2016 | Nyholm et al. |

\* cited by examiner

300 Anatomy is positioned in an imaging area of a computed tomography imaging apparatus

302 Virtual positioning model of the anatomy being imaged is shown by a means for showing image information

304 Location of the volume of the anatomy in the virtual positioning model desired to get imaged is pointed, selected or determined

306 Relation of position of a set of coordinates of the virtual positioning model to position of X-ray imaging means of the computed tomography imaging apparatus is resolved

308 Control information is transmitted to control system of the computed tomography imaging apparatus for imaging the volume of the anatomy desired to be imaged

Fig. 5

COMPUTED TOMOGRAPHY AND POSITIONING OF THE ANATOMY DESIRED TO BE IMAGED

FIELD OF INVENTION

The invention relates to positioning a volume to be imaged for computed tomography imaging or, to put it in other words, directing imaging to a desired anatomy. The invention particularly relates to the computed tomography imaging of the human or animal cranial area.

BACKGROUND OF INVENTION

Medical computed tomography imaging (CT imaging) is a form of X-ray imaging in which a volume to be imaged is irradiated from different directions and, from the data thus acquired, a desired two- or three-dimensional image is reconstructed afterwards. When X-ray imaging a person, the imaging must be implemented by as small a radiation dose as possible to still enable diagnosis Due to this, one e.g. tries to keep the size and shape of the volume to be imaged as small as possible. For example, it is typical for dental cone-beam computed tomography (CBCT) that it does not produce image information of an anatomy for reconstructing a cross section of volume of a width of a complete skull but to reconstruct only a smaller partial volume, such as one covering a portion of a dental arch. Wishing to image a certain partial volume but simultaneously trying not to image anything diagnostically inessential naturally causes a problem of positioning the anatomy being imaged to the imaging apparatus such that specifically the desired volume of the anatomy can be imaged.

It is known to use in positioning of the anatomy e.g. various positioning lights, such as laser lines. Aligning such lights to a desired point in the anatomy always takes some time and, when the whole process is based mostly on 'educated guess' on the position of the volume desired to be imaged in relation to the external features of the anatomy, the positioning by even an experienced person can prove to having been inaccurate. In such cases, it is possible that the imaging must be renewed, which increases the patient's total radiation dose and is in general frustrating and requires extra time from both the patient and the personnel.

It is also known to facilitate directing of the imaging by taking a scout X-ray image of the anatomy by a small radiation dose, from which image the location of the volume desired to get imaged can be identified. However, the quality of such scout images is typically quite poor and, on the other hand, even a small extra radiation dose does in any case always increase the radiation load.

BRIEF DESCRIPTION OF INVENTION

The object of the invention is to improve positioning of an anatomy for computed tomography imaging.

The invention as defined in the attached independent patent claims bases on a solution in which a virtual three-dimensional positioning model, being based on shapes of the surface of the anatomy being imaged, is shown on a display and utilized as a positioning tool. The volume of the anatomy desired to get imaged can be pointed, selected or defined from the positioning model. Some preferable embodiments of the invention are presented in the attached dependent claims and described in more detail in the following.

The invention is thus based on a solution in which a patient is positioned in the imaging area of a computed tomography imaging apparatus and a virtual positioning model generated of the patient being imaged is shown on a computer display or a display arranged in connection with the imaging apparatus. The positioning model can be e.g. a surface model generated based on optical imaging of the patient. In such a model, it is possible to point or select a volume desired to get imaged after which, information on the position of that volume is transmitted as control data to a control system of the computed tomography imaging apparatus. For the control system to know which volume in the set of coordinates of the imaging apparatus the volume selected from the display corresponds to, the system also includes information on how the set of coordinates of the model shown on the display is positioned in relation to the position of the X-ray image means of the computed tomography imaging apparatus. One solution for providing this data is to produce information for generating the virtual positioning model by optical means which are arranged as a part of the structure of the computed tomography imaging apparatus, whereby the generation of the positioning model and the actual CT imaging can be performed by the same apparatus and the same patient positioning.

The solution according to the invention provides a new kind of visual and easy-to-use possibility to direct the volume getting imaged at a desired place in the patient's anatomy and in a way which does not increase radiation load. The display utilized in directing the imaging can be placed in a separate space protected from radiation and the directing can be performed from there whereby, after the directing, there is no need to remain waiting for the person assisting the imaging to exit from the imaging set, for shelter from radiation.

BRIEF DESCRIPTION OF FIGURES

The invention is now described in more detail in reference to its preferable embodiments and the attached drawings, of which:

FIG. 5 shows one method according to the invention for positioning an anatomy for computed tomography imaging.

DETAILED DESCRIPTION OF INVENTION

Figure 1:
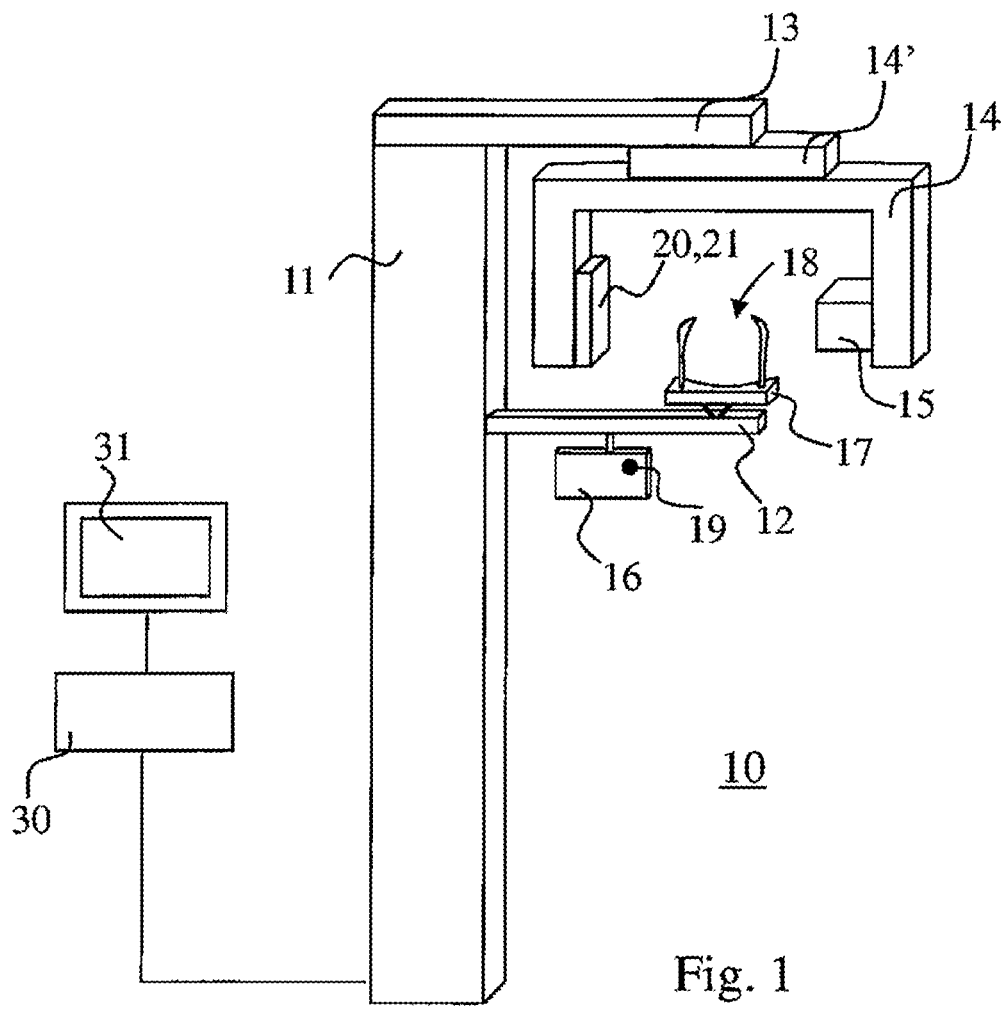
FIG. 1 shows a typical apparatus used in cone-beam computed tomography imaging.

FIG. 1 shows a basic structure of one apparatus suitable for use in computed tomography. The apparatus includes a vertical support construction 11 from which horizontally extends an arm 12 supporting patient support means and an arm part 13 which supports a structure supporting imaging means of the apparatus, an arm part 14. In the structure according to FIG. 1, the arm part 14 supporting the imaging means is arranged rotatable via a second rotatable arm part 14', which solution offers versatile possibilities for moving the imaging means. To the arm part 14 supporting the imaging means are arranged at a distance from each other an X-ray source 15 and a receiver of X-ray image information 21, which have been positioned to the apparatus with respect to a patient support means 17 such that to the apparatus is formed an imaging station 18 located between the X-ray source 15 and the receiver of X-ray image information 21 such that a beam produced by the X-ray source 15 can be aligned to pass via the imaging station 18 towards the receiver means of X-ray image information 21. The apparatus includes a control system of which FIG. 1 shows a control panel 16 arranged to the support construction 11 and an operating mode selection means 19 pertaining in it. In the apparatus according to FIG. 1, the receiver means of X-ray image information 21 are arranged as part of a receiver module of image information 20, which is arranged in a functional connection with a computer 30 via e.g. a fixed or wireless connection, such as a cable, Bluetooth or wireless network. To the computer are arranged means for processing image information and means for showing image information, which means include a display 31 for showing images generated by the computer.

Figure 2:
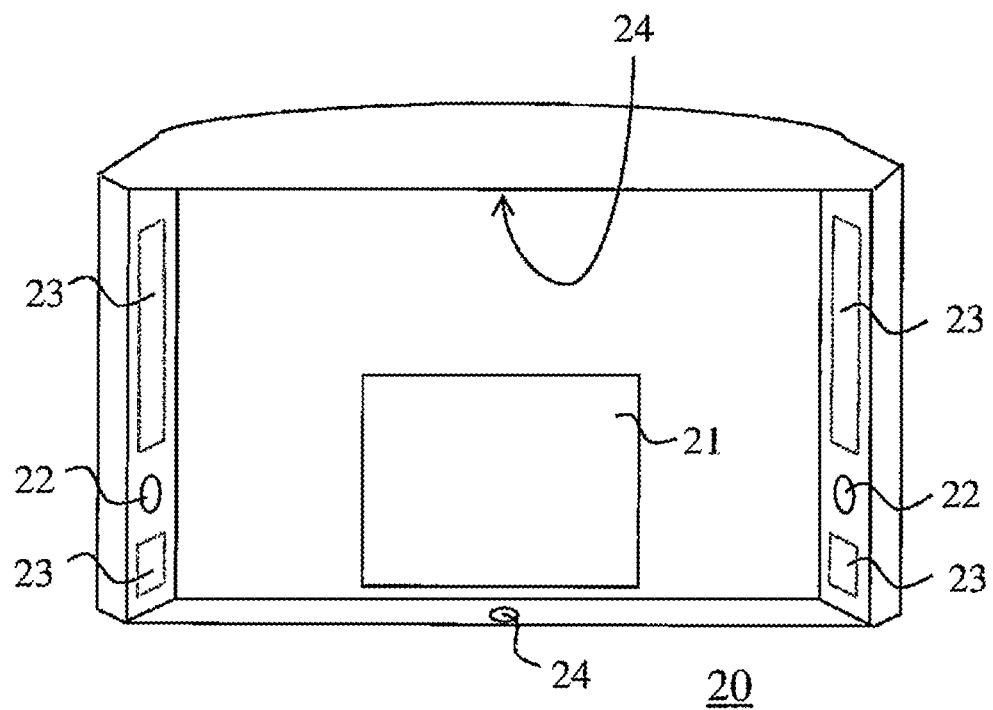
FIGS. 2 and 3 show a first and a second example of a receiver module of image information suitable for use in the apparatus according to FIG. 1.

FIG. 2 shows one receiver module of image information 20 applicable for use in the apparatus according to FIG. 1. The module includes two optical cameras 22 arranged horizontally on opposite sides of the X-ray detector 21 and aligned at the imaging station 18. Further, two lasers 24 are arranged to the module 20, as well as light sources 23 preferably producing white light to illuminate the imaging station 18 and. The lasers are positioned substantially in the middle of the module 20 to the substantial proximity of its upper and lower edges. The lasers 24 are arranged to emit and direct at the imaging station 18 a narrow vertical fan beam which casts a laser light pattern on the patient's face.

The light sources 23 can be arranged to produce lights of other color or colors than white. It is also possible to arrange to the apparatus more than two or only one camera 22, and the cameras or camera 22 can be arranged to operate not only as a photographic camera but also as a continuously-operating video camera. The light pattern to be cast on the patient's face can be produced by some other light source than a laser and the color of this light pattern, too, can be arranged changeable and, when produced by a laser, its color can be some other than the conventional red, such as preferably particularly green.

Figure 4:
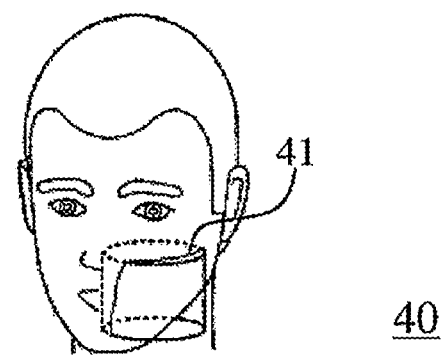
FIG. 4 shows a virtual positioning model and a positioning volume to be shown in connection with it.

A module of the type described above can be implemented by accommodating only a part of the above-mentioned components in it. As an example of a different module, FIG. 4 shows an arrangement which includes no lasers 24 but which pertains cameras 22 on top of each other to form a camera pair on both edges of the module 20. Still, there can be cameras 22 in either direction and even more than two.

FIG. 4 shows a virtual positioning model 40 of an anatomy and a positioning volume 41 shown in connection with it. The positioning volume 41 shown in FIG. 4 is a cylinder but it may also be of some other shape. In a situation where a portion of the positioning volume 41 is located outside and a portion inside the surface of the positioning model 40, it is possible to arrange the positioning volume 41 to be presented looking different for these parts.

It is also possible to show at least two positioning models 40 which show the anatomy from different projection directions and, if in that case also the positioning volume 41 is shown, it is also possible to show its location in relation to the positioning model 40 in each projection as seen from the corresponding direction.

FIG. 5 presents a method for directing computed tomography imaging to a desired volume of an anatomy being imaged. The method can utilize e.g. an arrangement shown in FIG. 1, which comprises a computed tomography imaging apparatus including X-ray imaging means, a control system of the computed tomography imaging apparatus, and a means for showing image information arranged in a functional connection with the computed tomography imaging apparatus. The computed tomography imaging apparatus can be e.g. a computed tomography apparatus (CT) or a cone-beam computed tomography imaging apparatus (CBCT). The means for showing image information can comprise e.g. a display 31, such as the display of a computer, a phone or a tablet. The display can be e.g. a conventional one or a touch screen.

In the method in step 300, an anatomy is positioned in the imaging area of the imaging apparatus, e.g. in the case of the apparatus shown in FIG. 1, in the patient support means 17 of the imaging station 18. The means for showing image information, such as the display 31, shows in step 302 the virtual positioning model 40 generated of the anatomy being imaged. The positioning model 40 can be e.g. a three-dimensional surface model or a three-dimensional volume model which comprises at least a portion of a cranial anatomy. The positioning model 40 can also be a texture model. The positioning model 40 can be generated in advance before positioning the patient in the imaging area, whereby it can be saved e.g. in the computer memory and then be acquired from there upon imaging. On the other hand, if suitable means, such as a module according to FIG. 3 or 4, has been arranged to the computed tomography apparatus, it is possible to generate the positioning model 40 when the anatomy to be imaged has been positioned in the imaging area of the computed tomography imaging apparatus. When in step 304 the location of the volume of the anatomy in the positioning model 40 desired to get imaged has been pointed, in step 306 the relation of the position of the set of coordinates of the positioning model 40 to the position of the X-ray imaging means of the computed tomography imaging apparatus is determined, whereby in step 308 one can transmit control data to the control system of the computed tomography imaging apparatus for imaging the desired volume of the anatomy. If the positioning model has been generated from image information acquired from the tomographic imaging apparatus in connection with a tomographic imaging event, the relation of the above-mentioned positions can be directly resolved from the known geometry of the components of the imaging apparatus and their calibration data. Step 306 can be carried out in the process already earlier than only after step 304. If the process utilizes a positioning model generated earlier or generated in some other way than from image information acquired by the tomography apparatus itself, a calibration arrangement is required for positioning the positioning model to the known set of coordinates of the computed tomography imaging apparatus.

Figure 3:
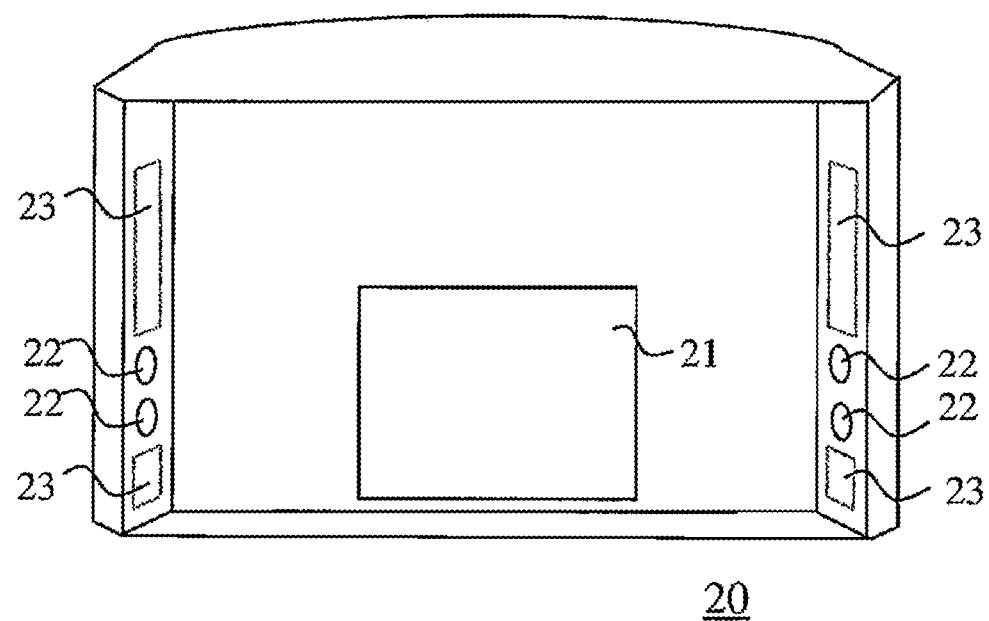

The positioning model 40 can thus be generated by an apparatus according to FIG. 1, for example, which comprises a module such as the one according to FIG. 2 or 3, in which apparatus, the structure 14 supporting the imaging means is arranged rotatable. Then, it is possible to take pictures of an anatomy positioned at the imaging station 18 by an optical camera arrangement of the receiver module of image information 20 from different directions and, in one possible arrangement, of a laser or some other light pattern projected on the anatomy. When using e.g. the arrangement according to FIG. 2, in which the cameras 22 and the lasers 24 are positioned at a distance from each other, it is possible to scan with the laser line the anatomy positioned at the imaging station 18 and, at the same time, take pictures of the anatomy at an angle with respect to the direction of the laser beam. From thus acquired image information, it is possible to generate a three-dimensional surface model to be used as the positioning model 40, which can be shown on the display 31.

The volume desired to get imaged can be pointed in the positioning model 40 e.g. by means of a computer mouse, a keyboard and/or by pointing the desired point directly on the display 31. It is possible to facilitate the pointing by showing on the display 31 a positioning volume 41 which can be moved. By means of the position volume, the location of the volume desired to get imaged in the positioning model 40 can be pointed or determined. The positioning volume 41 can be of the shape of e.g. a cylinder and correspond by its dimensions the volume the imaging apparatus is arranged to image. In one embodiment, the dimensions of the positioning volume 41 can be changed, which change is then communicated to the control system of the imaging apparatus.

To sum up, the method according to the invention for positioning an anatomy for computed tomography imaging can be described as a method in which an arrangement is used which comprises a computed tomography imaging apparatus including X-ray imaging means, a control system of the computed tomography imaging apparatus and a means for showing image information arranged in a functional connection with the computed tomography imaging apparatus. In the method, an anatomy including a volume desired to get imaged is positioned in the imaging area of the computed tomography imaging apparatus and a virtual positioning model is shown by the means for showing image information, the positioning model showing at least a portion of a three-dimensional surface of the anatomy and comprising the volume desired to get imaged. The location of the volume desired to get imaged is pointed, selected or determined in the virtual positioning model and, when the relation of a position of a set of coordinates of the virtual positioning model to a position of a set of coordinates of the X-ray imaging means of the computed tomography imaging apparatus has been resolved, control information is transmitted to the control system of the computed tomography imaging apparatus for imaging the volume of the anatomy desired to get imaged—which control information is thus based on the knowledge of the relation of the position of the set of coordinates of the virtual positioning model to the position of the set of coordinates of the X-ray imaging means of the computed tomography imaging apparatus and knowledge of the location in the positioning model of the volume desired to get imaged.

To facilitate the method, the means for showing image information can show a positioning volume, such as a volume comprising a cylinder surface, by means of which the location of the volume in the virtual positioning model desired to get imaged can be pointed, selected or determined. The dimensions of the positioning volume can be determined in advance or they can also be changeable. At least one of actions i) moving the anatomy in the imaging area, ii) moving the volume desired to get imaged shown on the means for showing image information, iii) moving the X-ray imaging means, may be included in the pointing, selecting or determining the position of the volume to get imaged. E.g. in a case in which the imaging apparatus according to FIG. 1 is utilized, in which the position of the rotation axis of the arm part 14 supporting the imaging means is freely adjustable within its operational range, there typically is no need for moving either the anatomy or the imaging means before the imaging but the imaging can be implemented starting from an original positioning but then implementing the actual imaging—i.e. the motions during the imaging—in accordance with the determination made on the display by means of the positioning model 40, whereby specifically the desired anatomy can be imaged.

When the anatomy has been positioned in the imaging area of the computed tomography imaging apparatus, the positioning model can be generated in real-time and it can also be updated while the anatomy being imaged is positioned in the imaging area of the computed tomography imaging apparatus. Hence, e.g. by utilizing an optical camera arrangement, it is possible to use the relation of the set of coordinates of the positioning model to the position of the imaging means of the computed tomography imaging apparatus to identify the position of the patient in the imaging area during computed tomography imaging and, if the position of the anatomy is noticed to change, the motion of the X-ray imaging means during the imaging is controlled by correcting their motion in a way corresponding the change in the position of the patient, i.e. to compensate for the change occurred in the patient's position.

The positioning model can thus be a model based on optical information, and information for the generating thereof can be produced by an optical camera arrangement arranged in the computed tomography imaging apparatus. The camera arrangement can be moved with respect to the anatomy being imaged in at least first motion direction and it can comprise i) a camera arrangement in which at least two optical cameras are positioned at a distance from each other in said motion direction or ii) at least two camera arrangements according to structure i) positioned at a distance from each other, in a substantially perpendicular direction with respect to said motion direction.

The method can be preferably applied in connection with imaging a cranial area, such as portions of the dental arch, whereby the virtual positioning model comprises at least a portion of the patient's cranial anatomy.

The positioning model can also be generated in advance before positioning the anatomy in the imaging area of the computed tomography imaging apparatus for computed tomography imaging, whereby the position of its set of coordinates in relation to the position of the set of coordinates of the X-ray imaging means of the computed tomography imaging apparatus can be made to correspond the position of the anatomy positioned in the imaging area of the computed tomography imaging apparatus in relation to the position of the set of coordinates of the X-ray imaging means of the computed tomography imaging apparatus.

The computed tomography imaging apparatus again can be described as comprising an x-ray imaging means which includes an X-ray source and a receiver means of image information, an imaging station, a control system, a means arranged in a functional connection with the computed tomography imaging apparatus for processing image information as well as a means for showing image information. The control system of such an apparatus comprises:

a means for showing on said means for showing image information a virtual positioning model, the positioning model showing at least a portion of a three-dimensional surface of an anatomy being imaged and comprising a volume desired to get imaged from said anatomy, a means for pointing, selecting or determining a position of the volume desired to get imaged in said virtual positioning model, a means for determining the relation of a position of a set of coordinates of said virtual positioning model to a position of a set of coordinates of the imaging means of the computed tomography imaging apparatus, and a means for transmitting to the control system of the computed tomography imaging apparatus control information for imaging said volume of the anatomy desired to get imaged, which control information is based on knowledge of the relation of the position of the set of coordinates of said virtual positioning model to the position of the set of coordinates of the X-ray imaging means of the computed tomography imaging apparatus and knowledge of the position of said volume desired to get imaged in said virtual positioning model.

Preferably, the control system of the apparatus comprises a means for showing on said means for showing image information a positioning volume by means of which the location of the volume in said position model desired to get imaged is pointed, selected or determined.

Furthermore, the control system may comprise a means for adjusting at least one of the following: the position of the positioning volume, one or more dimensions of the positioning volume, the position of the X-ray imaging means.

The apparatus can also comprise an optical camera arrangement and its control system a means for generating the positioning model from information produced by said optical camera arrangement. Such a camera arrangement can comprise e.g. i) a camera arrangement in which at least two optical cameras are positioned at a distance from each other in a first direction or ii) at least two camera arrangements according to structure i) positioned at a distance from each other in a substantially perpendicular direction with respect to said first direction.

Various features of the invention may have been described above in part in a more general terms or as a part of an imaging process while it is clear that features of the invention the implementation of which relates to structures or functions of an imaging apparatus, such as functions implemented according to a configuration of a control system, pertain in the features of an imaging apparatus according to the invention.

It is obvious for those skilled in the art that when technology advances, the basic idea of the invention may be implemented in many different ways. The invention and its embodiments are thus not limited by the examples described above but they may vary within the scope of the patent claims.

The invention claimed is:

1. A method for positioning an anatomy for computed tomography imaging, in which method, an arrangement is used which comprises a computed tomography imaging apparatus including X-ray imaging means, a control system of the computed tomography imaging apparatus and a means for showing image information arranged in a functional connection with the computed tomography imaging apparatus, in which method an anatomy including a volume desired to get imaged is positioned in the imaging area of the computed tomography imaging apparatus, a virtual positioning model is shown by said means for showing image information, the positioning model showing at least a portion of a three dimensional surface of said anatomy and comprising the volume desired to get imaged, a location of the volume in said virtual positioning model desired to get imaged is pointed, selected or determined, a relation of a position of a set of coordinates of said virtual positioning model to a position of a set of coordinates of the X-ray imaging means of the computed tomography imaging apparatus is resolved, control information is transmitted to the control system of the computed tomography imaging apparatus for imaging said volume of the anatomy desired to get imaged, which control information is based on knowledge of the relation of the position of the set of coordinates of said virtual positioning model to the position of the set of coordinates of the X-ray imaging means of the computed tomography imaging apparatus and knowledge of the location in said virtual positioning model of said volume desired to get imaged.

2. A method according to claim 1, wherein said means for showing image information also shows a positioning volume, by means of which the location of said volume in said position model desired to get imaged is pointed, selected or determined.

3. A method according to claim 2, wherein said positioning model comprises a cylinder surface.

4. A method according to claim 2, wherein when a part of the positioning volume is located outside the surface of the positioning model and a part inside the surface of the positioning model, for those parts, the positioning volume is presented looking different.

5. A method according to claim 1, wherein at least two positioning models are shown which show said anatomy from different projection directions, whereby in the case of also the positioning volume is shown, also its position in relation to the positioning model can be shown in connection with each positioning model as seen from the corresponding direction.

6. A method according to claim 2, wherein the dimensions of said positioning volume are determined in advance and/or are changeable.

7. A method according to claim 1, wherein said virtual positioning model is generated in real-time when the anatomy has been positioned in said imaging area of the computed tomography imaging apparatus and/or wherein said virtual positioning model is updated in real-time while the anatomy being imaged is positioned in said imaging area of the computed tomography imaging apparatus.

8. A method according to claim 1, wherein the pointing, selecting or determining of the location of said volume desired to get imaged comprises at least one of actions i) moving the anatomy in said imaging area, ii) moving the volume desired to get imaged shown on said means for showing image information, iii) moving the X-ray imaging means.

9. A method according to claim 1, wherein said virtual positioning model is a surface model or wherein said virtual positioning model is a volume model.

10. A method according to claim 1, wherein said virtual positioning model is a model based on optical information.

11. A method according to claim 10, wherein information for generating said virtual positioning model is produced by an optical camera arrangement arranged to the computed tomography imaging apparatus.

12. A method according to claim 11, wherein information for generating said virtual positioning model is produced by an arrangement which is moved with respect to the anatomy being imaged in at least first motion direction and which comprises i) a camera arrangement in which at least two optical cameras are positioned at a distance from each other in said motion direction or ii) at least two camera arrangements according to structure i) positioned at a distance from each other in a substantially perpendicular direction with respect to said motion direction.

13. A method according to claim 11, wherein said optical camera arrangement and said relation of the set of coordinates of the virtual positioning model to the position of the imaging means of the computed tomography imaging apparatus are utilized for identifying the position of the patient in the imaging area during computed tomography imaging and, if the position of the anatomy is noticed to change, the motion of said X-ray imaging means is controlled during the imaging to compensate for the change in the position of the patient.

14. A method according to claim 1, wherein said virtual positioning model comprises at least a portion of a patient's cranial anatomy.

15. A method according to claim 1, wherein said virtual positioning model is generated in advance before positioning the anatomy in the imaging area of the computed tomography imaging apparatus for computed tomography imaging and wherein the relation of the position of the set of coordinates of the positioning model to the position of the set of coordinates of the X-ray imaging means of the computed tomography imaging apparatus is made to correspond the position of the anatomy positioned in the imaging area of the computed tomography imaging apparatus in relation to the position of the set of coordinates of the X-ray imaging means of the computed tomography imaging apparatus.

16. A computed tomography imaging apparatus which comprises an X-ray imaging means which includes an X-ray source and a receiver means of image information, an imaging station, a control system, a means arranged in a functional connection with the computed tomography imaging apparatus for processing image information as well as a means for showing image information, in which apparatus, the control system comprises: a means for showing on said means for showing image information a virtual positioning model, the positioning model showing at least a portion of a three-dimensional surface of an anatomy being imaged and comprising a volume desired to get imaged from said anatomy, a means for pointing, selecting or determining a location of the volume in said virtual positioning model desired to get imaged, a means for determining a relation of a position of a set of coordinates of said virtual positioning model to a position of a set of coordinates of the imaging means of the computed tomography imaging apparatus, and a means for transmitting control information to the control system of the computed tomography imaging apparatus for imaging said volume of the anatomy desired to get imaged, which control information is based on knowledge of the relation of the position of the set of coordinates of said virtual positioning model to the position of the set of coordinates of the X-ray imaging means of the computed tomography imaging apparatus and knowledge of the location of said volume in said virtual positioning model desired to get imaged.

17. An apparatus according to claim 16, wherein said control system comprises a means for showing on said means for showing image information a positioning volume, by means of which the location of said volume in said position model desired to get imaged is pointed, selected or determined.

18. An apparatus according to claim 16, wherein said control system comprises a means for adjusting at least one of the following: the position of said positioning volume; one or more dimensions of said positioning volume; the position of said X-ray imaging means.

19. An apparatus according to claim 16, which comprises an optical camera arrangement and said control system comprises a means for generating said positioning model from information produced by said optical camera arrangement.

20. An apparatus according to claim 19, wherein said camera arrangement comprises i) a camera arrangement in which at least two optical cameras are positioned at a distance from each other in a first direction or ii) at least two camera arrangements according to structure i) positioned at a distance from each other in a substantially perpendicular direction with respect to said first direction.

* * * * *